United States Patent [19]

Yamamoto et al.

[11] Patent Number: 5,077,256
[45] Date of Patent: Dec. 31, 1991

[54] SILVER CATALYST FOR PRODUCTION OF ETHYLENE OXIDE AND METHOD FOR MANUFACTURE THEREOF

[75] Inventors: Takeshi Yamamoto; Shinichi Nagase, both of Tokyo; Hirohiko Tanabe, Kawasaki, all of Japan

[73] Assignee: Nippon Shokubai Kagaku Kogyo Co., Ltd., Osaka, Japan

[21] Appl. No.: 467,828

[22] Filed: Jan. 19, 1990

[30] Foreign Application Priority Data

Jan. 24, 1989 [JP] Japan ................................. 1-13202

[51] Int. Cl.$^5$ ........................ B01J 21/12; B01J 23/50
[52] U.S. Cl. .................................................. 502/243
[58] Field of Search ........................................ 502/243

[56] References Cited

U.S. PATENT DOCUMENTS

| | | | |
|---|---|---|---|
| 2,194,602 | 3/1940 | Law et al. | 502/243 |
| 2,458,266 | 1/1949 | Heider et al. | 502/243 |
| 3,875,080 | 4/1975 | Bergmann et al. | 502/243 |
| 3,962,136 | 6/1976 | Nielsen et al. | 502/243 |
| 4,242,235 | 12/1980 | Cognion | 502/243 |
| 4,305,844 | 12/1981 | Vangermain et al. | 502/243 |
| 4,310,442 | 1/1982 | Vangermain et al. | 502/170 |

FOREIGN PATENT DOCUMENTS 247414 2/1987 European Pat. Off. .
0229465 7/1987 European Pat. Off. .

Primary Examiner—Carl F. Dees
Attorney, Agent, or Firm—Omri M. Behr

[57] ABSTRACT

A silver catalyst for the production of ethylene oxide having 5 to 25% by weight, based on the amount of a finished catalyst, of finely divided metallic silver and 0.001 to 0.05 gram equivalent weight of cesium per kg of the finished catalyst carried on an α-alumina carrier having the outer surface thereof and the surface of pores in said carrier coated with amorphous silica, and a method for production thereof by supporting finely divided metallic silver and cesium and then subjecting the supported carrier to a high temperature heat treatment in an inert gas at a temperature of 400° to 950° C.

16 Claims, No Drawings

SILVER CATALYST FOR PRODUCTION OF ETHYLENE OXIDE AND METHOD FOR MANUFACTURE THEREOF

BACKGROUND OF THE INVENTION

1. Field of the Invention:

This invention relates to a silver catalyst to be used for the production of ethylene oxide by the catalytic gas-phase oxidation of ethylene with molecular oxygen and to a method for the manufacture of the silver catalyst.

2. Description of the Prior Art:

The silver catalyst which is used in the commercial production of ethylene oxide by the catalytic gas-phase oxidation of ethylene with molecular oxygen is required, for satisfactory performance of the function thereof, to exhibit high selectivity and high activity and enjoy a long catalyst life as.

Various studies have been made to date for the purpose of improving the performance of the silver catalyst and consequently fulfilling the requirement and efforts have been made to improve carriers, reaction promoters, silver compounds and the like. Numerous reports convering published. U.S. Pat. No. 3,207,700 and Japanese Patent Publications SHO 43(1968)-13,137, SHO 45(1970)-21,373, SHO 45(1970)-22,419 and SHO 45(1970)-11,217, Japanese Patent Laid-Open SHO 56(1981)-89,843, U.S. Pat. Nos. 2,766,261, 3,172,893, and 3,664,970 are their examples. Most of them, however, concern pore distributions and specific surface areas of carriers.

In U.S. Pat. No. 2,125,333, there is a description to the effect that an alkali metal salt containing sodium or potassium and a metal salt thereof is used as an additive for the silver catalyst in the manufacture of ethylene oxide.

In U.S. Pat. No. 2,238,474, there is a description to the effect that sodium hydroxide improves the activity of the silver catalyst for the production of ethylene oxide and potassium hydroxide has an adverse effect upon the activity of the silver catalyst.

In U.S. Pat. No. 2,765,283, there is a description to the effect that the silver catalyst is improved by adding 1 to 2,000 ppm by weight of an inorganic chlorinated substance such as sodium chloride to the catalyst carrier before silver is deposited on the carrier.

In U.S. Pat. No. 2,799,687 there is a description to the effect that a halide such as sodium chloride or potassium chloride, used in an amount of 20 to 16,000 ppm, functions as an inhibitor and induces degradation of the activity of the silver catalyst.

In U.S. Pat. No. 4,007,135, there is disclosed a catalyst for the production of alkylene oxide, which catalyst contains copper, gold, zinc, cadmium, mercury, niobium, tantalum, molybdenum, tungsten, vanadium, or preferably chromium, calcium, magnesium, strontium, and/or more preferably barium, and preferably further an alkali metal, in an amount preceding the amount naturally present as an impurity or cement in the carrier and sufficient to manifest the action of a promoter.

In U.S. Pat. No. 4,168,247, there is disclosed a catalyst for the production of alkylene oxide, which catalyst contains silver deposited on a porous heat-resistant carrier possessing a specific surface area in the range of 0.05 to 10 m$^2$/g and further contains sodium and at least one other alkali metal selected from the group consisting of potassium, rubidium, and cesium in a promoting amount in excess of the amount naturally present as an impurity or a binding agent in the carrier.

In U.S. Pat. No. 4,278,562, there is disclosure to the effect that a catalyst for the production of an alkylene oxide is obtained by depositing silver and optionally sodium or lithium in the subsequent treatment, depositing thereon the salts of such alkali metals as potassium, rubidium, and cesium in conjunction with an amine and/or ammonia.

In Japanese Patent Laid-Open SHO 55(1980)-145,677, there is disclosed a silver catalyst which, as a catalyst for the reaction of oxidation, has silver and, when necessary, further an alkali metal component or an alkaline earth metal component deposited on a non-acidic carrier containing alumina, silica, and titania in a total amount of not less than 99% by weight, containing metal of the Groups Va, VIa, VIIa. VIII, Ib, and IIb of the Periodic Table of Elements in a total amount of less than 0.1% by weight, and assuming no acid color on exposure to methyl red having a pKa value of +4.8.

In Japanese Patent Laid-Open SHO 56(1981)-105,750, there is disclosed a silver catalyst for the production of ethylene oxide, which silver catalyst is prepared by impregnating a carrier using α-alumina as a principal component thereof and having a sodium content of not more than 0.07% by weight and a specific surface area in the range of 1 to 5 m$^2$/g with an impregnation having 0.001 to 0.05 gram equivalent per kg of complete catalyst, of a complex of an alkali metal with boron, a complex of an alkali metal with molybdenum, and/or a complex of an alkali metal with tungsten contained in a decomposable silver solution formulated to give a deposition ratio of 5 to 25% by weight based on the complete catalyst, and then heating and reducing or thermally decomposing the product of impregnation.

In Japanese Patent Laid-Open SHO 57(1982)-107,241, there is disclosed a silver catalyst for the production of ethylene oxide, which catalyst incorporates therein, besides silver, sodium (Na) as a cationic component and chlorine (Cl) as an anionic component in amounts such that the atomic ratio of Cl/Na will be less than 1.

In U.S. Pat. No. 4,415,476, there is disclosed a silver catalyst for the production of etylene oxide, which silver catalyst contains, besides silver, at least sodium and cesium as cationic components and hlorine as an anionic component.

In U.S. Pat. No. 4,368,144, there is disclosed a silver catalyst for the production of ethylene oxide, which silver catalyst contains metallic silver particles deposited in a ratio of 5 to 25% by weight based on complete catalyst on an α-alumina carrier having a sodium content of not more than 0.07% by weight and a specific surface area in the range of 0.5 to 5 m$^2$/g and 0.001 to 0.05 gram equivalent of at least one alkali metal or alkali metal compound per kg of the complete catalyst and in excess of the amount naturally present in the carrier.

Japanese Patent Laid-Open SHO 63(1988)-116,743 disclosed a silver catalyst for the production of ethylene oxide, containing at least sodium, potassium, rubidium, and/or cesium other than silver as cationic components, among other catalytic components, and using a carrier mainly comprising an α-alumina, having a surface area in the range of 0.6 to 2 m$^2$/g, a water absorption ratio in the range of 20 to 50%, a silica content in the range of 0.5 to 12% by weight, a silica content per surface area (% by weight/m$^2$/g) in the range of 0.5 to 12, preferably 1 to 8, and a sodium content in the range of 0.08 to 2% by weight.

Numerous silver catalysts have been proposed as described above. Most of them have their catalytic performance enhanced by incorporating in silver catalysts such amounts of alkalis as falling in restricted ranges. Though these catalysts manifest satisfactory initial catalytic performance, they are deficient in terms of service life.

Concerning the carrier of the silver catalyst to be used for the production of ethylene oxide, many points remain yet to be clarified and many problems still await better solutions. For example, the component substances of the carrier, such physical properties of the carrier as specific surface area, pore diameter, pore distribution, pore volume, porosity, particle diameter, and shape, and the chemical properties owned by the such materials for the carrier as $\alpha$-alumina, silicon carbide, silica, and zirconia have room for further improvements aimed at optimization.

An object of this invention, therefore, is to provide a novel silver catalyst for the production of ethylene oxide, which silver catalyst combines such qualities as high selectivity, high activity, and long service life, and a method for the production of the silver catalyst.

Another object of this invention is to provide a novel silver catalyst for the production ethylene oxide, which silver catalyst enjoys improved service life owing to the use of an $\alpha$-alumina carrier possessing a specific surface area in the range of 0.75 to 5 m$^2$/g and an apparent porosity in the range of 45 to 70%, and a method for the production of the silver catalyst.

SUMMARY OF THE INVENTION

The objects described above are accomplished by a silver catalyst for the production of ethylene oxide, which comprises having 5 to 25% by weight, based on the amount of a finished catalyst, of finely divided metallic silver and 0.001 to 0.05 gram equivalent weight of cesium per kg of the finished catalyst carried on an $\alpha$-alumina carrier having the outer surface thereof and the surface of pores in the carrier coated with amorphous silica by supporting finely divided metallic silver and cesium and then subjecting the supported carrier to a high temperature heat treatment in an inert gas at an elevated temperature in the range of 400° to 950° C.

These objects are further accomplished by a method for the production of a silver catalyst for the production of ethylene oxide comprising the steps of impregnating an $\alpha$-alumina carrier with an aqueous solution containing colloidal silica, then drying the impregnated $\alpha$-alumina carrier by heating, further calcining the dried $\alpha$-lamina carrier thereby preparing an $\alpha$-alumina carrier having the outer surface thereof and the surface of pores in the carrier coated with amorphous silica, causing 5 to 25% by weight, based on the amount of a finished catalyst, of finely divided metallic silver and 0.001 to 0.05 gram equivalent weight of cesium per kg of the finished catalyst to be carried on the $\alpha$-alumina carrier, activating the resultant composite thereby effecting deposition of the silver and the cesium on the resultant porous inorganic refractory carrier, and subsequently subjecting the composite to a high temperature heat treatment in an inert gas containing oxygen in a concentration of not more than 3% by volume at an elevated temperature in the range of 400° to 950° C.

By preparing an $\alpha$-alumina carrier having the outer surface thereof and the surface of pores in the carrier coated with amorphous silica and then causing 5 to 25% by weight, based on the amount of a finished catalyst, of finely divided metallic silver and 0.001 to 0.05 gram equivalent weight of cesium per kg of the finished catalyst to be carried on the $\alpha$-alumina carrier, this invention obtains a novel silver catalyst for the production of ethylene oxide, which silver catalyst is capable of retaining high selectivity and high activity over a long time.

EXPLANATION OF THE PREFERRED EMBODIMENT

Our study in search of a carrier suitable for use in a silver catalyst for the production of ethylene oxide has revealed that when an $\alpha$-alumina carrier having a specific surface area in the range of 0.075 to 5 m$^2$/g and apparent porosity in the range of 45 to 70% and having the outer surface thereof and the surface of pores in the carrier coated with amorphous silica is used rather than the carrier heretofore used generally on a commercial when it has a relatively high specific surface area and has never been used on a commercial scale in the field because of the insufficient selectivity exhibited by a catalyst produced with the carrier and the catalyst obtained by causing particularly cesium and/or a cesium compound to be carried as a reaction accelerator and silver and cesium and/or a cesium compound carried as an activating agent on the $\alpha$-alumina carrier, subjecting the resultant composite to an activating treatment cesium compound on the $\alpha$-alumina carrier, then high temperature heat-treating the composite in an inert gas containing oxygen in a concentration of not more than 3% by volume at an elevated temperature in the range of 400° to 950° C. exhibits high activity, high selectivity, and high durability never attained to date. The catalysts which are used in the production of ethylene oxide by the catalytic vapor-phase oxidation of ethylene with molecular oxygen are silver catalysts and, quite naturally, most of them are carried catalysts using a carrier. It is also known widely that the carriers used for these carried silver catalysts are porous particulate refractories.

The porous particulate refractory carrier, simple as it may be, is varied widely. The physical properties of carrier such as specific surface area, pore distribution, pore volume, particle diameter, and shape and the chemical properties owned by such component substances of carrier as $\alpha$-alumina, silica, silicon carbide, zirconia, and clay affect the produced catalysts in a large measure.

The selection of a carrier having a specific set of properties, therefore, poses itself a serious problem for persons engaging in the art. Among other properties, the specific surface area deserves particular attention because it bears also on pore diameter and affects the performance of a produced catalyst in a large measure. From the standpoint of activity and durability, the catalyst is preferable to have a large specific surface area and, for that reason, the carrier is preferable to have a large specific surface area. For the carrier to have a large specific surface area, the alumina particles to be selected as the material for the carrier are required to have a small diameter. This fact necessarily signifies formation of pores of a minute diameter. This fact proves to be disadvantageous from the standpoint of dispersion and retention of gas and removal of heat of reaction. It also entails a disadvantage that the area of the exposed surface of the carrier is consequently large. These factors invariably contribute to impairing the selectivity. In the light of all of these facts, the statement that the specific surface area is preferable to be large does not always hold good but have limits of its own. Most carriers heretofore employed on a commercial scale have specific surface areas not exceeding 1 $m^2/g$, even not exceeding 0.5 $m^2/g$. Exceptionally, some catalysts use carriers having specific surface areas exceeding 1 $m^2/g$. They, however, have lower selectivity than those using carriers of a lower specific surface area.

As a result of continuing a study in search of a solution to the disadvantage, we have found a method of permitting effective use of a carrier having a large specific surface area exceeding 0.75 $m^2/g$ without a sacrifice of selectivity and allowing a catalyst to be produced with further improved activity and durability. To be brief, this method is accomplished by the use of an $\alpha$-alumina carrier having the outer surface thereof and the surface of pores in the carrier coated with amorphous silica. The method is particularly effective in a carrier which possesses a large specific surface area of not less than 0.75 $m^2/g$ and also effective in an extended catalyst incorporating therein a cesium compound. It is an amazing fact that the disadvantage arising from the physical aspect of carrier is mended by the chemical quality of carrier ascribed to the coating of the outer surface of carrier and the surface of pores in the carrier with amorphous silica. The specific surface area reported in the present specification represents the value determined by the Brunauer-Emmett-Teller (hereinafter referred to as "BET") method.

In accordance with this invention, the outer surface of carrier and the surface of pores in the carrier delicately affect the performance of the produced catalyst and, in the case of a carrier possessing a specific surface area of not more than 0.5 $m^2/g$ and heretofore used generally in the field, this adverse effect of the aspect of the surfaces decreases in proportion as the specific surface area decreases and gradually increases beyond the level of 0.5 $m^2/g$ and increases conspicuously as the specific surface area exceeds 0.75 $m^2/g$. It has been now found that a carrier which possesses a specific surface area of not less than 0.75 $m^2/g$ and which has failed to find utility because of the insufficient selectivity exhibited by a catalyst produced with the carrier, i.e. an $\alpha$-alumina carrier using secondary alumina particles having a specific surface area in the range of 0.75 to 5 $m^2/g$, an apparent porosity in the range of 45 to 70%, and a particle diameter in the range of 50 to 100 microns, is not only usable in this invention but also excellent in activity and selectivity. As demonstrated clearly in the working examples cited hereinafter, an $\alpha$-alumina carrier having a specific surface area of about 0.89 $m^2/g$ is enabled by the coating of the outer surface thereof and the surface of pores therein with amorphous silica to have the difference in performance manifested in the service life of the catalyst produced by incorporation therein of cesium, though other properties of the carrier may be more or less responsible for the difference in quality. This is a surprising fact. The mechanism which underlies this unexpected improvement still defies our exact comprehension. The presence of amorphous silica in an amount in the prescribed range on the outer surface of carrier and on the surface of pores in the carrier has a beneficial effect. The catalyst produced by deposited thereby causing deposition of silver and cesium and/or a cesium compound on a porous inorganic refractory carrier, and then high temperature heat-treating the composite in an inert gas containing oxygen in a concentration of not more than 3% by volume at an elevated temperature in the range of 400° to 950° C. exhibits an improvement of about 2% in selectivity as compared with a comparative catalyst which has not undergone this heat treatment. Further, it is reported or silica hinges heavily on the status of pH. When all of these matters are taken into account, it is only logical to conclude that the presence of the amorphous silica on the outer surface of the carrier and the surface of pores in the carrier has a strong effect, as associated with the pH distribution within the carrier, on the deposition and distribution of silver and more of cesium. This fact is believed to bear upon the performance of the produced catalyst.

The amount of cesium and/or a cesium compound to be incorporated favorably in the catalyst of this invention is in the range of 0.001 to 0.05 gram equivalent weight, preferably 0.003 to 0.03 gram equivalent weight, and the most preferably in the range of more than 0.008 gram equivalent weight to 0.03 gram equivalent weight, per kg of finished catalyst.

The $\alpha$-alumina carrier of this invention is required to have a specific surface area in the range of 0.75 to 5 $m^2/g$, preferably 0.8 to 2 $m^2/g$, to be used effectively in the present invention. An $\alpha$-alumina carrier having a specific surface area of more than 5 $m^2/g$ is impractical because it fails to produce a substantially satisfactory catalyst. In addition to the $\alpha$-alumina and sodium component (mainly $Na_2O$), the carrier is preferable to contain such components in such amounts that are normal in the field of carrier.

The apparent porosity of the $\alpha$-alumina carrier of this invention is preferable to be in the range of 45 to 70%, more preferably 50 to 60%. The specific pore volume of the $\alpha$-alumina carrier of this invention is preferable to fall in the range of 0.1 to 0.8 cc/g, more preferably 0.2 to 0.5 cc/g. The $\alpha$-alumina carrier of this invention comprises preferably not less than 90% by weight of a main $\alpha$-alumina component having a particle diameter in the range of 3 to 20 mm, preferably 7 to 14 mm, and secondary alumina particles having a particle diameter in the range of 50 to 100 microns. The carrier to be used in the present invention is a particulate refractory carrier in the form of beads, pellets, or rings, whose average equivalent diameter is in the range of 3 to 20 mm, preferably 7 to 14 mm. The percentage composition of the components of the carrier and the specific surface area of the carrier bears heavily on the performance of the produced catalyst. The selection of a carrier so shaped as to permit easy uniform deposition thereon of silver and cesium and/or a cesium compound during the course of production of a catalyst is a prerequisite for successful production of a catalyst excelling in selectivity.

To be used advantageously in the present invention, the $\alpha$-alumina carrier is preferable to be produced by preparing an $\alpha$-alumina carrier comprising more preferably not less than 90% by weight of an $\alpha$-alumina component having a BET specific surface area in the range of 0.8 to 2 $m^2/g$, an apparent porosity in the range of 50 to 60%, a specific pore volume in the range of 0.2 to 0.5 cc/g, and particle diameter in the range of 3 to 20 mm, impregnating the $\alpha$-alumina carrier with a liquid having colloidal silica having a particle diameter in the range of 5 to 50 millimicrons, preferably 6 to 20 millimicrons dispersed in water of an amount equaling the impregnated α-alumina carrier by heating, and calcining the dried composite at a temperature in the range of 700° to 1,500° C., preferably 1.000° to 1,400° C., for a period in the range of 1 to 10 hours, preferably 2 to 6 hours. As a result of the treatment of this procedure, the produced α-alumina carrier has the outer surface thereof and the surface of pores therein coated with amorphous silica.

Advantageously, the α-alumina carrier of this invention is preferable to incorporate therein amorphous silica in a concentration in the range of $3 \times 10^{-4}$ to $2 \times 10^{-1}$ g, preferably $5 \times 10^{-4}$ to $1 \times 10^{-1}$ g, as Si per g of the carrier. The preparation of the catalyst is effected by a method which comprises impregnating the carrier described above with an aqueous solution or a solution in an organic solvent of a decomposable silver salt such as, for example, an aqueous silver nitrate solution, an ammonia complex of silver with an inorganic or organic acid, an amine complex of silver with an organic acid, or an aqueous silver lactate solution. The cesium and/or cesium compound may be deposited in advance on the carrier or deposited simultaneously with silver on the carrier by preliminary incorporation in the silver solution. Otherwise, it is may be deposited on the carrier on which silver has been already deposited after the step for decomposition and reduction of silver and the subsequent step for decomposition and reduction of silver and the subsequent step for decomposition and removal. Subsequently, the impregnated carrier is heated for decomposition or reduction of the decomposable silver salt. The product of this decomposition is then decomposed and removed by the use of a heated gas.

The salts of silver with inorganic and organic acids which are usable in this invention include silver nitrate, silver carbonate, silver sulfate, silver acetate, silver oxalate, silver lactate, silver succinate, and silver glucolate, for example.

The amine which are usable for the formation of the amine complex include alkanolamines such as mono-, di-, and tri- ethanolamines, mono-, di-, and tri-n-propanolamines, mono-, di-, and tri-isopropanolamines, and alkylamines such as n-butylamine and isobutylamine, for example.

Water is advantageously used as the solvent for the solution of a decomposable silver salt. The other solvents which are usable herein include lower aliphatic compounds of 2 to 6 carbon atoms having 1 to 3 alcoholic hydroxyl groups in the molecular unit, such as methanol, isopropanol, n-propanol, monoethylene glycol, diethylene glycol, triethylene glycol, trimethylene glycol, monopropylene glycol, methyl cellosolve, ethyl cellosolve, methyl carbitoal, ethyl carbitol, and glycerol, for example.

The cesium compounds which are usable herein include cesium oxalate, cesium carbonate, cesium acetate, and other salts, and oxides and hydroxides, for example.

It is important that the high temperature heat treatment should be carried out in an inert gas having containing molecular oxygen in a concentrations of not more than 3% by volume, preferably not more than 1%. Typical effective inert gases are nitrogen, helium, argon, carbon dioxide, neon, etc.

In the present invention, activation treatment means a heat treatment at a relatively low temperature, e.g. at least 150° C. to less than 400° C. in a molecular oxygen containing gas such as air for decomposing and dispersing an organic compound after precipitating and depositing the used silver compound and cesium compound in a conventional method for production of silver catalyst.

As concerns the preparation of the silver catalyst using the α-alumina catalyst contemplated by this invention, a silver catalyst to be used in the production of ehylene oxide by the catalytic vapor-phase oxidation of ethylene with molecular oxygen can be obtained by adopting a method which comprises preparing an α-alumina carrier of his invention, impregnating this α-alumina carrier with a solution of a decomposable silver such as an amine complex of silver with an organic acid, heating the impregnated α-alumina carrier to a temperature in the range of 100° C. to 300° C. thereby reducing or thermally decomposing the silver salt effecting deposition silver and cesium and/or a cesium compound on a porous inorganic refractory carrier, and finally high temperature heat-treating the resultant composite in an insert gas containing oxygen in a concentration of not more than 3% by volume at an elevated temperature in the range of 400° to 950° C., preferably 500° to 800° C.

In the silver catalyst of this invention, silver can be deposited on the surface of the carrier in the form of a fine powder in an amount in the range of 5 to 25% by weight, preferably 5 to 20% by weight, based on the amount of a finished catalyst. The cesium or the cesium compound may be deposited simultaneously with the silver or deposited separately either before or after the deposition of the silver. For any of these manners of deposition, the cesium or the cesium compound is added in the form of an aqueous solution or an alcohol form solution to the silver solution in a concentration in the range of 0.001 to 0.05 gram equivalent weight, preferably 0.003 to 0.03 gram equivalent weight, per kg of finished catalyst.

The reaction conditions heretofore known in the art are all usable in the production of ethylene oxide by the oxidation of ehylene with molecular oxygen in the presence of the silver catalyst of this invention. The reaction conditions generally employed in the production of ethylene oxide on a commercial scale can be used advantageously. Specifically, the ethylene content of the feed gas is in the range of 0.5 to 40% by volume, preferably 2 to 20% by volume, the oxygen content thereof in the range of 3 to 10% by volume, preferably 4 to 8% by volume, the carbon dioxide gas content in the range of 5 to 30% by volume, preferably 6 to 12% by volume, and the balance of such insert gases as nitrogen, argon, and steam, lower hydrocarbons such as methane and ethane, and halides such as ethylene dichloride and diphenyl chloride as reaction depressants. The spatial velocity of the feed gas is in the range of 1,000 to 30,000 $hr^{-1}$ (STP), preferably 1,000 to 10,000 $hr^{-1}$ (STP) and the pressure is in the range of 2 to 40 kg/cm² G, preferably 10 to 30 kg/cm² G.

Now, the present invention will be described more specifically below with reference to working examples and controls. It should be noted, however, that this invention is not limited to these examples but may be practiced otherwise without departing from the spirit of the invention.

The magnitudes of conversion and the selectivity reported in the working examples and controls were calculated in accordance with the following formulas.

$$\text{Conversion} = (\%) \frac{\text{Mol number of reacted ethylene}}{\text{Mol number of ethylene in feed gas}} \times 100$$

$$\text{Selectivity (\%)} = \frac{\text{Mol number of ethylene converted into ethylene oxide}}{\text{Mol number of reacted ethylene}} \times 100$$

Procedure for production of Carrier A

An $Al_2O_3$ (98 9% by weight in purity) carrier (produced by Norton Company and marketed under trademark designation of "Carrier SA-5102") having a BET specific surface area of 0.89 $m^2/g$, an apparent porosity of 52.8%, and a specific pore volume of 0.28 cc/g was impregnated with a liquid having colloidal silica 2 to 50 millimicrons in particle diameter dispersed in water of amount equaling the water content of carrier. The impregnated carrier was concentrated and dried by heating and calcined at 1,000° C. for four hours. Consequently, there was obtained an α-alumina carrier having a BET specific surface area of 0.89 $m^2/g$, an apparent porosity of 52.8%, and a pore volume of 0.28 cc/g and having the surface of pores in the carrier of $Al_2O_3$ (98,4% by weight) coated with amorphous silica. This α-alumina carrier was labeled as Carrier A. The amount of amorphous silica carried on Carrier A was found by the following method to be $5 \times 10^{-3}$ g of Si per g of carrier. [Method for determination of amount of amorphous silica on the outer surface of the carrier (Carrier A) and the surface of pores in the carrier]

A 10 g of the carrier was crushed to a size of 8 to 10 meshes, immersed for one hour in 20 ml of an aqueous 46% by weight hydrofluoric acid solution, and filtered. The filtrate was tested for Si ion content with an atomic absorption analyzer.

EXAMPLE 1

An impregnating solution was prepared by preparing a slurry containing 830 g of silver oxalate and 200 ml of water, adding this slurry to 700 ml of ethanolamine, stirring the resultant mixture thoroughly for solution of solids, thoroughly stirring the resultant solution and 100 ml of water added thereto, and then stirring the resultant solution with a solution of 14.2 g of cesium nitrate in 200 ml of water.

In this impregnating solution, 4,000 ml of the α-alumina carrier A, heated in advance to about 100° C. was left standing for impregnation. The impregnated carrier was concentrated and dried by heating, further heated in an air bath at 120° C. for three hours, and then activated in a current of air at 280° C. for 48 hours.

The catalyst thus obtained was packed in a closed container of stainless steel adapted to introduce an inert gas, swept with nitrogen gas, and heat-treated in an electric oven at a catalyst bed temperature of 600° C. for three hours, to obtain a finished catalyst. The total cesium content of the finished catalyst was found to be $11 \times 10^{-3}$ gram equivalent weight/kg of catalyst.

Method for determination of total cesium content of finished catalyst

A sample, about 20 g, was pulverized and rolled (with a pressure of 20 kg/$cm^2$) to prepare a test sheet. A catalyst of a known cesium content was similarly treated to prepare a standard test sheet. The test sheet was evaluated by the use of a calculation graph obtained from a record data of the standard sample with a fluorescent X-ray spectral analyzer. The finished catalyst was consequently found to have a total cesium content of $11 \times 10^{-3}$ gram equivalent weight/kg of catalyst.

The finished catalyst thus obtained was packed in an externally heating double-pipe length. To the packed bed of the finished catalyst, a mixed gas containing 20% by volume of ethylene, 7% by volume of oxygen, 7% by volume of carbon dioxide gas, and the balance of methane, nitrogen, argon, and ethane and 1 ppm of ethylene dichloride was introduced to induce a reaction under the conditions of reaction pressure of 24 Kg/$cm^2$ G, The results of 10 days reaction and those of one year's reaction were as shown in Table 1.

EXAMPLE 2

A reaction was performed by following the procedure of Example 1, except that the heat treatment was carried out under the conditions shown in Table 1. The results of 10 days' reaction and those of one year's reaction were as shown in Table 1.

EXAMPLES 3 and 4

A reaction was performed by following the procedure of Example 1, except that carriers indicated in Table 1 were used instead. The results of 10 days' reactions and these of one year's reactions were as shown in Table 1.

Controls 1 and 2

A reaction was performed by following the procedure of Example 1, except that the high temperature heat treatment was carried out under the conditions indicated in Table 1. The results of 10 days' reaction were as shown in Table 1.

Control 3

A reaction was performed by following the procedure of Example 1, except that the carrier (produced by Norton Company and marketed under trademark designation of "Carrier SA-5102") was used in its unmodified form. The results of 10 days' reaction were as shown in Table 1.

Control 4

A reaction was performed by following the procedure of Example 1, except that the carrier (produced by Norton Company and marketed under trademark designation of "Carrier SA-5102") was used in its unmodified form and the cesium content was changed as shown in Table 1 and the heat treatment was omitted. The results of 10 days' reaction and those of one year's reaction were as shown in Table 1.

Control 5

A reaction was performed by following the procedure of Example 1, except that the cesium content was changed as shown in Table 1 and the high temperature heat treatment was omitted. The results of 10 days' reaction and those of one year's reaction were as shown in Table 1.

Control 6

A reaction was performed by following the procedure of Example 1, except that the high temperature heat treatment was carried out in air instead of nitrogen atmosphere. The 10 days' reaction was as shown in Table 10.

TABLE 1

| | Example | | | | Control | | | | | |
|---|---|---|---|---|---|---|---|---|---|---|
| | 1 | 2 | 3 | 4 | 1 | 2 | 3 | 4 | 5 | 6 |
| <Properties of carrier> | | | | | | | | | | |
| Specific surface area (m$^2$/g) | 0.89 | 0.89 | 0.89 | 0.89 | 0.89 | 0.89 | 0.89 | 0.89 | 0.89 | 0.89 |
| Apparent Porosity (%) | 52.8 | 52.8 | 52.8 | 52.8 | 52.8 | 52.8 | 52.8 | 52.8 | 52.8 | 52.8 |
| Specific pore volume (cc/g) | 0.28 | 0.28 | 0.28 | 0.28 | 0.28 | 0.28 | 0.28 | 0.28 | 0.28 | 0.28 |
| <Composition> | | | | | | | | | | |
| Al$_2$O$_3$ (% by weight) | 98.4 | 98.4 | 98.9 | 89.9 | 98.4 | 98.4 | 98.9 | 98.9 | 98.4 | 98.4 |
| Amount of amorphous silica in finished catalyst (g as Si/g of carrier) | $5 \times 10^{-3}$ | $5 \times 10^{-3}$ | $5 \times 10^{-4}$ | $1 \times 10^{-1}$ | $5 \times 10^{-3}$ | $5 \times 10^{-3}$ | $1.5 \times 10^{-4}$ | $1.5 \times 10^{-4}$ | $5 \times 10^{-3}$ | $5 \times 10^{-3}$ |
| Ratio of deposition of silver in finished catalyst (% by weight) | 9 | 9 | 9 | 9 | 9 | 9 | 9 | 9 | 9 | 9 |
| Amount of cesium in finished catalyst (gram equivalent weight/kg of catalyst) | $11 \times 10^{-3}$ | $22 \times 10^{-3}$ | $11 \times 10^{-3}$ | $11 \times 10^{-3}$ | $11 \times 10^{-3}$ | $11 \times 10^{-3}$ | $11 \times 10^{-3}$ | $3 \times 10^{-3}$ | $3 \times 10^{-3}$ | $11 \times 10^{-3}$ |
| Temperature of heat treatment (°C.) | 600 | 700 | 600 | 600 | — | 300 | 600 | — | — | 500 |
| Time of heat treatment (hours) | 3 | 3 | 3 | 3 | — | 3 | 3 | — | — | 3 |
| Atmosphere of heat treatment | N$_2$ | N$_2$ | N$_2$ | N$_2$ | N$_2$ | N$_2$ | N$_2$ | N$_2$ | N$_2$ | air |
| <Reaction conditions> | | | | | | | | | | |
| (after 10 days) | | | | | | | | | | |
| Reaction temperature (°C.) | 233 | 233 | 233 | 233 | No reaction | No reaction | No reaction | 230 | 230 | 245 |
| Conversion (%) | 10 | 10 | 10 | 10 | | | | 10 | 10 | 10 |
| Selectivity (%) | 81 | 81 | 80.5 | 80.5 | | | | 78.5 | 79.0 | 79.0 |
| (after 1 year) | | | | | | | | | | |
| Reaction temperature (°C.) | 235 | 235 | 235 | 235 | — | — | — | 235 | 235 | 235 |
| Conversion (%) | 10 | 10 | 10 | 10 | | | | 10 | 10 | 10 |
| Selectivity (%) | 80.5 | 80.5 | 79.8 | 80.0 | | | | 76.5 | 77.0 | 77.0 |

What is claimed is:

1. A silver catalyst for the production of ethylene oxide which comprises having 5 to 25% by weight, based on the amount of a finished catalyst, of finely divided metallic silver and 0.001 to 0.05 gram equivalent weight of cesium per kg of the finished catalyst carried on an α-alumina carrier having the outer surface thereof and the surface of pores in said carrier coated with amorphous silica by supporting finely divided metallic silver and cesium and then subjecting the supported carrier to a high temperature heat treatment in an inert gas at an elevated temperature in the range of 400° C. to 950° C.

2. A catalyst according to claim 1, wherein said α-alumina carrier contains said amorphous silica in an amount in the range of $3 \times 10^{-4}$ to $2 \times 10^{-1}$ g as Si per g of carrier.

3. A catalyst according to claim 1, wherein said α-alumina carrier possesses an apparent porosity in the range of 45 to 70%.

4. A catalyst according to claim 1, wherein the amount of said cesium to be carried is in the range of 0.003 to 0.03 gram equivalent weight per Kg of the finished catalyst.

5. A catalyst according to claim 2, wherein said coating with said amorphous silica is accomplished by dispersing colloidal silica having a particle diameter in the range of 5 to 50 millimicrons in water of an amount equaling the water content of carrier, impregnating said α-alumina carrier with the resultant dispersion, and drying and calcining the impregnated carrier.

6. A catalyst according to claim 4, wherein said α-alumina carrier contains said amorphous silica in an amount in the range of $5 \times 10^{-4}$ to $1 \times 10^{-1}$ g as Si per g of carrier.

7. A catalyst according to claim 3, wherein said α-alumina carrier possesses a BET specific surface area in the range of 0.75 to 5 m$^2$/g, a specific porosity in the range of 0.1 to 0.8 cc/g, and a particle diameter in the range of 3 to 20 mm.

8. A catalyst according to claim 2, wherein the amount of silver to be carried is in the range of 5 to 25% by weight.

9. A method for the production of a silver catalyst for the production of ethylene oxide, characterized by the steps of impregnating an α-alumina carrier with an aqueous solution containing colloidal silica, then drying the impregnated α-alumina carrier by heating, further calcining the dried α-alumina carrier thereby preparing an α-alumina carrier having the outer surface thereof and the surface of pores in said carrier coated with amorphous silica, causing 5 to 25% by weight, based on the amount of a finished catalyst, of finely divided metallic silver and 0.001 to 0.05 gram equivalent weight of cesium per Kg of the finished catalyst to be carried on said α-alumina carrier, activating the resultant composite thereby effecting deposition of said silver and said cesium on the resultant porous inorganic refractory carrier, and subsequently subjecting the composite to a high temperature heat treatment in an inert gas containing oxygen in a concentration of not more than 3% by volume at an elevated temperature in the range of 400° to 950° C.

10. A method according to claim 9, wherein said α-alumina carrier contains said amorphous silica in an amount in the range of $3 \times 10^{-4}$ to $2 \times 10^{-1}$ g as Si per g of carrier.

11. A method according to claim 9, wherein said α-alumina carrier possesses an apparent porosity in the range of 45 to 70%.

12. A method according to claim 9, wherein the amount of said cesium to be carried is in the range of 0.003 to 0.03 gram equivalent weight per Kg of finished catalyst.

13. A method according to claim 10, wherein said coating with said amorphous silica is accomplished by dispersing colloidal silica having a particle diameter in the range of 5 to 50 millimicrons in water or an amount equaling the water content of carrier, impregnating said α-alumina carrier with the resultant dispersion, and drying and calcining the impregnated carrier.

14. A method according to claim 12, wherein said α-alumina carrier contains said amorphous silica in an amount in the range of $5 \times 10^{-4}$ to $1 \times 10^{-1}$ g as Si per g of carrier.

15. A method according to claim 11, wherein said α-alumina carrier has a BET specific surface area in the range of 0.75 to 5 m$^2$/g, a specific porosity in the range of 0.1 to 0.8 cc/g, and a particle diameter in the range of 3 to 20 mm.

16. A method according to claim 10, wherein the amount of silver to be carried out in the range of 5 to 25% by weight.

* * * * *